(12) United States Patent
Marmur et al.

(10) Patent No.: US 12,357,778 B2
(45) Date of Patent: Jul. 15, 2025

(54) MOBILE INHALER AND A CONTAINER FOR USING THEREWITH

(71) Applicant: SkyX IP Holdings I LLC, New York, NY (US)

(72) Inventors: Abraham Marmur, Haifa (IL); Philippe Lacour-Gayet, Bel Ombre (MU); Julien Lacour-Gayet, Lacroix-sur-Lutry (CH); Dror Nedivi, Petach Tikva (IL); Francesco Guidetti, Chernex (CH); Zeev Shpiro, Tel-Aviv (IL)

(73) Assignee: SKYX IP HOLDINGS I LLC, New York, NY (US)

( * ) Notice: Subject to any disclaimer, the term of this patent is extended or adjusted under 35 U.S.C. 154(b) by 0 days.

(21) Appl. No.: 17/407,061

(22) Filed: Aug. 19, 2021

(65) Prior Publication Data

US 2022/0040423 A1 Feb. 10, 2022

Related U.S. Application Data

(63) Continuation of application No. 15/770,735, filed as application No. PCT/IL2017/050402 on Apr. 3, 2017, now abandoned.

(30) Foreign Application Priority Data

Apr. 4, 2016 (EP) ..................................... 16163666
Jun. 28, 2016 (EP) ..................................... 16176635
(Continued)

(51) Int. Cl.
*A61M 15/06* (2006.01)
*A24F 40/05* (2020.01)
(Continued)

(52) U.S. Cl.
CPC ............. *A61M 15/06* (2013.01); *A24F 40/05* (2020.01); *A24F 40/30* (2020.01); *A24F 40/42* (2020.01);
(Continued)

(58) Field of Classification Search
CPC .......... A61M 15/0003; A61M 15/0021; A61M 15/06; A61M 11/001; A61M 11/042;
(Continued)

(56) References Cited

U.S. PATENT DOCUMENTS

| 5,435,282 A | 7/1995 | Haber |
| 5,518,179 A * | 5/1996 | Humberstone ..... B05B 17/0684 239/102.2 |

(Continued)

FOREIGN PATENT DOCUMENTS

| DE | 102006041042 | 3/2008 |
| EP | 0718046 | 6/1996 |

(Continued)

*Primary Examiner* — Timothy A Stanis
(74) *Attorney, Agent, or Firm* — Caldwell Intellectual Property Law (57) ABSTRACT

A mobile inhaler is provided and a container for using therewith. The mobile inhaler comprises: a mouthpiece comprising at least one inhaling opening; a body element connected to the mouthpiece and comprising a housing for holding a DC power source; a power conversion unit comprising an inverter operative to convert a DC voltage provided by a DC power source, into a higher AC voltage; a nebulizer comprising an ultrasonic vibrator and a mesh, wherein the ultrasonic vibrator is activated by the AC voltage, and wherein the nebulizer is adapted to enable converting into aerosol droplets at least part of a liquid comprised in an enclosure, and the aerosol droplets to be directly inhaled from the mouthpiece; and an enclosure adapted to enable holding a liquid, and characterized in that (Continued)

it provides a connection to enable fluid transfer from the enclosure to the nebulizer.

20 Claims, 7 Drawing Sheets

(30) Foreign Application Priority Data

Sep. 7, 2016 (EP) .................................... 16187618
Feb. 7, 2017 (EP) .................................... 17155046

(51) Int. Cl.

| | |
|---|---|
| *A24F 40/30* | (2020.01) |
| *A24F 40/42* | (2020.01) |
| *A24F 40/44* | (2020.01) |
| *A24F 40/51* | (2020.01) |
| *A61M 11/00* | (2006.01) |
| *A61M 11/04* | (2006.01) |
| *A61M 15/00* | (2006.01) |
| *A24F 40/10* | (2020.01) |
| *A24F 40/49* | (2020.01) |
| *A61M 16/00* | (2006.01) |
| *A61M 16/10* | (2006.01) |

(52) U.S. Cl.

CPC .............. *A24F 40/44* (2020.01); *A24F 40/51* (2020.01); *A61M 11/001* (2014.02); *A61M 11/005* (2013.01); *A61M 11/007* (2014.02); *A61M 11/042* (2014.02); *A61M 15/0003* (2014.02); *A61M 15/0021* (2014.02); *A61M 15/0085* (2013.01); *A24F 40/10* (2020.01); *A24F 40/49* (2020.01); *A61M 15/009* (2013.01); *A61M 2016/0024* (2013.01); *A61M 2016/0027* (2013.01); *A61M 16/1085* (2014.02); *A61M 2202/0488* (2013.01); *A61M 2205/123* (2013.01); *A61M 2205/276* (2013.01); *A61M 2205/3576* (2013.01); *A61M 2205/3584* (2013.01); *A61M 2205/3592* (2013.01); *A61M 2205/50* (2013.01); *A61M 2205/581* (2013.01); *A61M 2205/583* (2013.01); *A61M 2205/60* (2013.01); *A61M 2205/6018* (2013.01); *A61M 2205/6072* (2013.01); *A61M 2205/8206* (2013.01)

(58) Field of Classification Search

CPC . A61M 11/005; A61M 15/0085; A24F 40/05; A24F 40/30; A24F 40/42; A24F 40/44
See application file for complete search history.

(56) References Cited

U.S. PATENT DOCUMENTS

| | | | | |
|---|---|---|---|---|
| 6,014,970 | A | 1/2000 | Ivri et al. | |
| 6,196,218 | B1 * | 3/2001 | Voges | B05B 17/0607 128/200.14 |
| 8,333,187 | B2 | 12/2012 | Gallem | |
| 9,352,108 | B1 * | 5/2016 | Reed | A61M 15/0091 |
| 2002/0129812 | A1 * | 9/2002 | Litherland | B05B 17/0646 128/200.14 |
| 2003/0010336 | A1 * | 1/2003 | Vito | B65D 83/303 128/200.22 |
| 2004/0206351 | A1 | 10/2004 | McFarland | |
| 2005/0011514 | A1 | 1/2005 | Power | |
| 2007/0222463 | A1 | 9/2007 | Qahoug | |
| 2008/0173729 | A1 * | 7/2008 | Weng | B06B 1/0253 239/102.2 |
| 2009/0050142 | A1 | 2/2009 | Hamano | |
| 2009/0095821 | A1 | 4/2009 | Feriani | |
| 2010/0044460 | A1 | 2/2010 | Sauzade | |
| 2011/0168194 | A1 | 7/2011 | Hon | |
| 2011/0265806 | A1 | 11/2011 | Alarcon | |
| 2012/0266870 | A1 | 10/2012 | Denyer | |
| 2012/0291776 | A1 * | 11/2012 | Van Der Mark | A61M 15/0001 128/200.14 |
| 2013/0079732 | A1 * | 3/2013 | Burt | B08B 3/12 604/290 |
| 2013/0267864 | A1 | 10/2013 | Addington | |
| 2016/0213866 | A1 * | 7/2016 | Tan | A61M 15/0021 |
| 2016/0361506 | A1 | 12/2016 | Lin | |
| 2017/0127722 | A1 | 5/2017 | Davis | |
| 2017/0202266 | A1 | 7/2017 | Sur | |
| 2017/0238608 | A1 * | 8/2017 | Matsumoto | A24F 40/42 |
| 2017/0368273 | A1 * | 12/2017 | Rubin | A61M 16/0093 |
| 2018/0289907 | A1 | 10/2018 | Marmur | |
| 2018/0289908 | A1 | 10/2018 | Marmur | |
| 2019/0015612 | A1 | 1/2019 | Marmur | |

FOREIGN PATENT DOCUMENTS

| | | | |
|---|---|---|---|
| EP | 2886185 | | 6/2015 |
| EP | 2523710 | | 10/2015 |
| GB | 2524856 | | 10/2015 |
| KR | 100877433 | | 1/2009 |
| WO | WO9707896 | A1 | 3/1997 |
| WO | WO2001085240 | | 11/2001 |
| WO | 2010078428 | A1 | 7/2010 |
| WO | WO2014167515 | | 10/2014 |
| WO | WO2015092757 | | 6/2015 |
| WO | WO2015101760 | | 7/2015 |
| WO | WO2015179002 | | 11/2015 |
| WO | WO2016076178 | | 5/2016 |

* cited by examiner

MOBILE INHALER AND A CONTAINER FOR USING THEREWITH

CROSS-REFERENCE TO RELATED APPLICATIONS

This application is a continuation of U.S. patent application Ser. No. 15/770,735, filed Apr. 24, 2018, which is a national stage application under 35 U.S.C. § 371 of International Application No. PCT/IL2017/050402, filed Apr. 3, 2017. International Application No. PCT/IL2017/050402 claims priority from European Patent Applications 17155046.0, filed Feb. 7, 2017, 16187618.0, filed Sep. 7, 2016, 16176635.7, filed Jun. 28, 2016 and 16163666.7, Apr. 4, 2016. The disclosure of each of these referenced applications is incorporated by reference herein in its entirety.

TECHNICAL FIELD

The present disclosure relates to inhalers for delivering substances to the respiratory system of a user and in particular to inhalers which deliver the substance in the form of an aerosol of droplets.

BACKGROUND

An inhaler is a medical device used for delivering substance (e.g. medication) into the body via the lungs.

Several types of inhalers are known in the art. The most common type of inhaler is the pressurized metered-dose inhaler (MDI). In MDIs, medication is typically stored in solution in a pressurized canister that contains a propellant, although it may also be a suspension. The MDI canister is attached to a plastic, hand-operated actuator. On activation, the metered-dose inhaler releases a fixed dose of medication in aerosol form. The aerosolized medication is drawn into the lungs by continuing to inhale deeply before holding the breath for few seconds to allow the aerosol to settle onto the airways of the lung. Another type is the dry powder inhaler that releases a metered or device-measured dose of powdered medication that is inhaled through the device. A nebulizer is a further type of inhaler that typically supplies the medication as an aerosol created from an aqueous formulation.

One of the issues addressed by the present invention is the provisioning of a novel inhaler which, among others, allows a user to inhale nicotine, by overcoming various problems associated with smoking cigarettes or smoking e-cigarettes.

Cigarette smoking is associated with combustion of tobacco as well as other compounds, which generate up to 5000 different combustion products and are known to be the major cause for different diseases including chronical obstructive pulmonary diseases (COPD), cancer and cardiovascular diseases. It is the combustion that creates harmful and potentially harmful chemical compounds.

In the last decade, a new way of nicotine consumption has started to gain popularity, the so-called e-cigarettes or Electronic Nicotine Delivery System (ENDS).

In an e-cigarette or ENDS in general, a liquid composition containing nicotine, propylene glycol, vegetable glycerine and flavorings, is evaporated by means of heating a coil surrounding a wick. The wick is a fabric (usually cotton) through which liquid is drawn by capillarity. When the coil (being an electrical resistance) surrounding the wick is connected to power source, it heats the liquid to temperatures of up to about 300° C., thereby causing the vaporization of the liquid contained in the wick, and the user then inhales this vapour.

Although an e-cigarette or ENDS has recently been recognized as being a safer alternative to a tobacco cigarette (e.g. Public Health England recognising that e-cigarettes are 95% less risky than combustible tobacco), there are still different disadvantages linked with the use of e-cigarettes.

Due to the fact that the liquid composition is being vaporized, traces of toxic or potentially toxic compounds might still be produced when an e-cigarette is used, through various heat-induced chemical reactions. The vapor can contain toxicants and traces of heavy metals (at levels permissible in inhalation medicines), and potentially harmful chemicals not found in tobacco smoke. To a lesser extent, some materials used in e-cigarettes (metals and plastics) may generate additional harmful chemical compounds when the temperature is elevated.

SUMMARY OF THE DISCLOSURE

The disclosure may be summarized by referring to the appended claims.

It is an object of the present invention to provide a solution that overcomes the drawbacks of the prior art devices.

It is another object of the present invention to provide a device for nicotine and/or nicotine replacement which does not lead to generation of toxic or potentially toxic compounds and which nevertheless will generate droplets with a size suitable for penetrating deeply into the lung.

It is another object of the present invention to provide a device where the traditional heat-based coil is replaced by a mesh type nebulizer which does not only suppresses all heat induced chemical reactions in the liquid, but also delivers an aerosol with measurable, small and possibly controlled droplet size, which in turn allows targeted delivery that is particularly suited for the use in oral drug delivery.

Other objects of the present disclosure will become apparent from the following description and the disclosure may be summarized by referring to the appended claims.

According to a first embodiment of the present disclosure, there is provided a mobile inhaler, comprising:

a mouthpiece comprising at least one inhaling opening;

a body element connected to the mouthpiece and comprising a housing for holding a DC power source (e.g. a battery);

a power conversion unit comprising an inverter operative to convert a DC voltage provided by a DC power source, into a higher AC voltage;

a nebulizer comprising an ultrasonic vibrator and a mesh, wherein the ultrasonic vibrator is activated by the AC voltage, and wherein the nebulizer enables converting at least part of a liquid composition comprised in an enclosure into aerosol droplets, which are directly inhaled from the mouthpiece; and an enclosure adapted to enable holding a liquid composition, characterized in that it provides a connection to enable fluid transfer from the enclosure to the nebulizer.

The present invention relates to a body element that is connected to the mouthpiece. It should be understood that the term "connected" as used herein, encompasses both a case where the body element and the mouthpiece are two distinct parts which are connected or connectable to each other, as well as a case where the body element and the mouthpiece are two portions of a single integral element.

Replacing the traditional heating element (e.g. a coil) by a mesh type nebulizer not only suppresses heat induced chemical reactions associated with the liquid composition, but also delivers an aerosol with measurable, small droplet size, which in turn allows delivery of the substance comprised in the droplets, deep in the lung.

In accordance with another embodiment, the enclosure of the mobile inhaler includes a mechanism that enables fluid transfer from the enclosure to the nebulizer, irrespective of a spatial angle at which the mobile inhaler is being handheld.

According to a further embodiment, the liquid composition comprised in the mobile inhaler enclosure is in a contact with a wick.

In accordance with another embodiment, the wick is in a contact with the nebulizer mesh, thereby preventing direct contact between the mesh and the liquid composition comprised within the mobile inhaler's enclosure.

According to still another embodiment, the mobile inhaler is configured to enable inhaling aerosol droplets derived from over 60% of an initial volume of the liquid composition held within the mobile inhaler's enclosure.

According to another embodiment, the mouthpiece is detachably connected to the body element. Optionally, the nebulizer is comprised within the mouthpiece. This option has the advantage that, since the mouthpiece and the nebulizer may need to be replaced from time to time, the mouthpiece for hygienic reasons, and the mesh if a large enough number of its holes are clogged, a replacement of the mouthpiece and the nebulizer can occur in a single step. In addition, this embodiment eliminates the need to handle separately the relatively small nebulizer.

In accordance with another embodiment, the mesh is fixedly positioned in the mobile inhaler, and the ultrasonic vibrator enables conveying liquid held in the enclosure towards the mesh (i.e. a passive mesh).

The nebulizer having a passive mesh, preferably comprises a transducer horn connected to a piezo-electric ultrasound vibrator. The transducer horn has preferably a longitudinal round cross-section and in particular a longitudinal cross section profile that converges towards its free vibrating end. The free vibrating end face of the transducer preferably has the same shape of the mesh. In particular, the diameter of the free vibrating end face of the transducer horn corresponds to the diameter of a round shaped mesh. In addition, the transducer horn is preferably located in the body element of the mobile inhaler and the mesh is attached to a container that is detachably associated with the mobile inhaler.

The passive mesh is preferably made of a metal sheet. Alternatively, the plate may be made of a plastic material or of a fabric.

Preferably the mesh is attached to that container at the lower end of the inhaling channel which is located adjacent to the transducer horn when the inhaler is assembled.

By another embodiment, the mesh comprised in the nebulizer is operable by activating the ultrasonic vibrator (i.e. an active mesh).

In accordance with another embodiment, the active mesh comprises a plurality of openings and a dome-shaped portion. Optionally, one or more of the plurality of openings are tapered openings. The tapering is positioned in the flow direction of the liquid composition. That means that according to this option, the opening cross section where droplets are generated is smaller than the opening cross section where the liquid composition is provided.

A nebulizer having an active mesh may include a vibrating plate attached to the ultrasonic vibrator (e.g. a piezo-electric vibration generator) such that the vibrating plate is vibrated when the ultrasonic vibrator is activated.

According to another embodiment, the active mesh is preferably adapted to be vibrated at the resonance frequency of the nebulizer. More preferably to be vibrated at a frequency of up to 250 KHz.

By still another embodiment, the mesh comprises a plurality of openings, and wherein at least two of the openings included among the plurality of openings, are different from each other (e.g. having at least one dimension which is different from each other).

Additionally, the dome-shaped portion of the active mesh may be arranged such that the convex side of a vibrating plate is arranged on the side of the inhaling opening of the mouthpiece.

The mesh may have openings with a diameter between 700 and 8000 nanometres, preferably, between 2500 and 3000 nanometres. In addition, as described above the mesh may have openings with different diameters, thereby enabling formation of different droplet sizes by using the same mesh plate.

The active mesh is preferably made of a metal sheet. Alternatively, the plate may be made of a plastic material or of a fabric.

According to a further embodiment, the mobile inhaler further comprises an electrical circuit for increasing AC voltage provided to the ultrasonic vibrator. Optionally, the electrical circuit enables controlling an amount of liquid converted into aerosol droplets, by changing the level of the AC voltage provided. For example, by changing the voltage provided to the ultrasonic vibrator, the amplitude of the vibrations of the mesh is changed and consequently the nebulizer output is controlled, i.e. the amount of aerosol droplets nebulized within a given time interval.

The DC voltage of the power source is a power that can be provided by using one or more batteries (e.g. 3.7V) and is converted into a higher AC voltage (e.g. between 75 and 200 Vpp with a frequency between 100 kHz and 200 kHz).

Since the power source is likely to be subjected to a voltage drop over time when a battery is used, optionally, a voltage controller may be used in order to maintain the voltage delivered by the power source to be essentially constant over time, e.g. within a 5% tolerance range.

According to another embodiment, the electrical circuit comprises a resonant circuit.

By still another embodiment, the electrical circuit comprises a phase-locked loop (PLL). In case that the nebulizer is operated at its resonance frequency, the use of the PLL has an advantage that it is able to maintain the nebulizer in resonance even if there is a resonance frequency shift due e.g. to the liquid characteristics, wear or clogging of the nebulizer.

In accordance with a further embodiment, the mobile inhaler also comprises a vacuum sensor configured to affect the operation of the mobile inhaler. For example, the vacuum sensor may control the amount of aerosol being inhaled by a user of that mobile inhaler. Also, the amount of liquid composition converted into aerosol droplets may depend on the vacuum level at the mobile inhaler.

The vacuum sensor may be connected or connectable to a control unit of the mobile inhaler for activating the nebulizer upon using the mobile inhaler, i.e. upon inhalation through the mouthpiece by a user.

According to an embodiment, while the mobile inhaler is used, a user generates a vacuum through inhaling from the mouthpiece. With a vacuum sensor, the nebulizer of the inhaler is automatically activated. By following this embodiment, there is no need for the user to turn on the nebulizer by taking a further action, such as e.g. pressing a button. Further, as the nebulizer is only activated upon inhaling, battery is not wasted as the nebulizer is only operated when a user is inhaling.

According to an embodiment, the control unit is configured to activate the nebulizer depending on a pressure difference detected by the vacuum sensor, in order to correlate the nebulizer aerosol output with the pressure difference. Thus, in the case where the substance used is nicotine or an agent for a nicotine replacement therapy (NRT), the user is provided with a realistic smoking feeling, comparable to the feeling of smoking a real cigarette since the nebulizer aerosol output is adapted to the inhalation intensity.

According to still another embodiment, the mobile inhaler further comprises a heating means adapted to enable increasing aerosol temperature prior to its egress via the mouthpiece. The heating means may be configured to ensure that the inhaled aerosol is heated up to a predetermined temperature, while ensuring that no change occurs in the chemical properties of the substance being inhaled. The predetermined temperature is less than 100° C., and preferably it is one that is comfortable for the user body, e.g. 37° C.±4° C.

In addition or optionally, the heating means are adapted to heat the liquid composition included in the container, prior to having it nebulized.

The heating means may be for example a heating coil or an electric powered heat exchanger.

By yet a further embodiment, the mouthpiece is movable between a rest position and a use position, wherein in the rest position, the mouthpiece is at least partially accommodated into the body element.

In accordance with another embodiment, the mobile inhaler further comprises a communication interface for transferring and/or receiving information between the mobile inhaler and a remote electronic device. The communication interface may be the same interface as the one used for charging (e.g. a micro USB port) if applicable, or may be an interface that allows communications over a wireless connection operative in compliance with a communication standard such as Wi-Fi or Bluetooth.

The information exchanged between the mobile inhaler and the remote electronic device, may typically relate to the consumption of the liquid composition by the user. However, it may also be used for remote programming of a control unit of the mobile inhaler in any one of various cases. Examples are: to ensure that a user only inhales a pre-defined amount of the agent/compound comprised in the liquid composition during a given time interval, monitoring the user (patient) compliance with a pre-defined therapeutic regime, etc.

According to still another embodiment, the mobile inhaler further comprises audio and/or visual means for providing information to a user of the mobile inhaler. This information may be a low battery indication alerting the user that a power source should be recharged or replaced. Such a low battery indication may optionally be in a form of causing the nebulizer to reduce the aerosol output, e.g. by reducing the amplitude of the vibration of the nebulizer mesh. Additionally, or in the alternative, a low battery indication may be in the form of a LED being lighted, a sound may be generated and/or vibrations may be generated.

Other indications that may be provided when the audio and/or visual means operate are for example a low level of the container content and/or liquid level, operational problems that relate to the mobile inhaler, etc.

According to another embodiment, the mobile inhaler further comprises locking means to prevent unauthorized use of the mobile inhaler. For example, preventing children from using the mobile inhaler, or inhaling a medicinal composition by users other than the user for whom the medicinal composition was intended, etc.

The locking means may be for example a user identification device, such as s fingerprint reader. In the alternative, the locking means may comprise a switch that should be twisted while simultaneously inhaling, in order to enable operation of the device.

By yet another embodiment, the liquid is comprised in a container (e.g. a capsule) which is detachably associated with (e.g. insertable into) the enclosure of the mobile inhaler. One option of carrying out this embodiment is by using a body element which is detachably connected to the mouthpiece, to allow easier opening and closing of the housing (the enclosure) and replacement of the container.

As would be understood by those skilled in the art, the enclosure of the mobile inhaler may be such that it may be configured to hold the liquid composition either directly by enabling the addition of the liquid composition to a pre-defined volume comprised within the enclosure, or indirectly by holding a container (e.g. a capsule) in which the liquid composition is comprised.

By yet another embodiment, the container is located at least partially inside the mouthpiece and is disposable. For example, the mouthpiece may be such that the major part of the container (over 50% of its volume) is placed within the mouthpiece. In the alternative, the container is completely placed inside the mouthpiece.

The at least one inhaling opening of the mouthpiece is designed for directing an aerosol flow preferably towards the palate and/or the tongue of a user, in order to increase the sensory experience. The mouthpiece may be designed in a shape and size that are selected so as to allow mouth-only inhalation. The mouthpiece has preferably a total inhaling opening area between 50% and 300% of the area of the mesh which is provided with openings. The area of the mesh provided with openings is meant in the context of the present invention as the smallest area of a surface which can enclose all the openings of the mesh.

According to a further embodiment, the nebulizer mesh is comprised in the container.

According to another embodiment, the mobile inhaler further comprises a resilient means operative to enable biasing the container and/or the nebulizer towards each other. Preferably, the container is biased towards the nebulizer. Biasing may be achieved by using a spring arranged in order to push the container and/or the nebulizer towards each other.

By yet another embodiment, the container (which is detachably associated with the enclosure) or the enclosure itself, includes a piston. This embodiment may be used for example in order allow continuous supply of liquid to the mesh.

In accordance with still another embodiment, the mobile inhaler further comprises a communication interface for receiving information stored in the container which is detachably associated with the mobile inhaler.

According to another embodiment, the mobile inhaler further comprises one or more additional enclosures for holding at least one additional liquid, or for holding at least one additional container comprising at least one additional liquid. Obviously, depending on the user's needs, the mobile inhaler may contain three or more containers.

One possible substance that may be comprised in an additional container is a substance for discharging a required aroma.

Optionally, a second container which is adapted to be held by the second enclosure, may comprise a mesh type nebulizer, for nebulizing the second liquid.

Optionally, the mobile inhaler may further comprise a vaporizer operative to vaporize one or more of the at least one additional liquid. One way to implement this embodiment is when a nebulizer associated with a second enclosure/container is a heating coil vaporizer for vaporizing the liquid comprised in the second enclosure/container. Alternatively, the second enclosure/container includes a heating coil vaporizer for vaporizing the liquid comprised therein. A further alternative is using a spray nozzle as the second nebulizer, when the second container comprises the second liquid and a propellant gas.

It should be noted that the first and the second nebulizers may be operated simultaneously and/or in sequence and/or independently, in accordance with the inhalation requirements.

According to an embodiment, the mouthpiece of a mobile inhaler comprising at least two nebulizers is provided with two inhaling channels, each having an inhaling opening, each of the inhaling channels being assigned to one of the first and second enclosures such that mixing of the aerosol from the first enclosure with the aerosol or vapour of the second enclosure happens in the user's mouth.

By still another embodiment, the mobile inhaler of further comprises a control unit adapted to control the operation of the mobile inhaler. The control unit may be configured for example to control operation of said mobile inhaler in accordance with a predefined medication provisioning scheme.

Optionally, the control unit is adapted to control the voltage and/or frequency of the current provided to the nebulizer.

In addition, the control unit may optionally comprise means to enable retrieving information stored at a container which is detachably associated with the mobile inhaler. The retrieval of the information may be done over RFID or an optical readable code or an electronic memory (e.g. as in a credit card) associated with the capsule. This information may relate to the content of the container (e.g. substance, concentration, liquid amount, etc.) and is used by the control unit to operate the inhaler. As an example, if a daily dose limit is pre-determined for a user, the control unit may be used to establish if the dose limit has been already reached by evaluating the consumption of the solute comprised in the liquid composition.

The information exchanged may also include instruction(s) for the user that relate to the liquid composition included in the container. Such information may include the type of liquid composition (e.g. type of medicine), dose and a consumption pattern to be applied. Once the information is retrieved from the container by the mobile inhaler, it may be self-programmed in order to comply with the way by which the mobile inhaler should operate in accordance with that information.

Optionally, the control unit may be configured not only to control the operation of the mobile inhaler (e.g. triggering the nebulizer, forwarding data to a remote device, reading information associated with the capsule), but also as a device that can be used for planning the usage of the mobile inhaler (e.g. frequency and intensity of inhaling), and may trigger generating alerts on the mobile inhaler and/or at other remote devices (e.g. a mobile phone, PDA) in order to alert the user that it is time for him/her to use the mobile inhaler, and/or to inform the user that the capsule (container) content is about to be consumed and that a new capsule should be inserted, and/or that his/her use of the inhaler is too frequent, etc.

In addition, the control unit may be configured to enable provisioning of power for operating the nebulizer for a pre-defined period of time.

According to another aspect of the invention there is provided a container (e.g. a capsule) for use by an inhaler (i.e. the user of the inhaler), wherein the container comprises a liquid composition that includes a physiological solution and at least one solute (e.g. a supplement).

Thus, such a container is receptacle of a housing associated with the inhaler, for example, a housing which is associated with a mouthpiece of the inhaler.

In accordance with another embodiment of this aspect of the invention, the container further comprises an electronic storage configured to store data that relates to at least one member of the group that consists of: information that relates to the liquid composition held within the container, information that relates to a user that is about to consume the liquid composition being held within the container, instructions that relate to consumption of the liquid composition being held within the container, any combination thereof, and the like.

By still another embodiment of this aspect of the invention, the liquid composition comprised in the container includes at least 80% water, for example at least 92% water.

According to another embodiment, the physiological solution is a normal saline solution containing about 0.9% w/v NaCl.

According to yet another embodiment of this aspect of the invention, the at least one solute is a member selected from a group that consists of: nicotine, a compound suitable for nicotine replacement therapy, a product obtained by filtering a liquid through tobacco, a medicinal drug, an aroma agent, a surfactant, a viscosity enhancer, an agent operative to dilate respiratory airways of a user of the inhaler, and any combination thereof.

In case that the at least one solute is an aroma agent, the content of the aroma agent in liquid composition should preferably be less than or equal to about 2% w/w.

In case that the at least one solute is a surfactant, it is preferably selected from a group that consists of: anionic surfactants, non-ionic surfactants, cationic surfactants, amphoteric or zwitterionic surfactants, polymeric surfactants or surface active polymers. Preferably, the surfactant content is not higher than 1% w/w of the liquid composition.

In case that the at least one solute is a viscosity enhancer, preferably, its content is not higher than 1% w/w of the liquid composition. Such a viscosity enhancer may be for example fructose.

By balancing the content of components of the liquid composition, in particular the viscosity enhancer and the electrolyte, compositions with different characteristics and properties may be provided. For example, it is possible to decrease the visible aerosol that is exhaled by a user, thus making the composition suitable for use in enclosed spaces (offices, public transport, restaurants, airplanes, etc.) where normal smoking is usually prohibited.

In a case where the at least one solute is a medicinal drug, it may be a pain killer, medical cannabis, an antibiotic, and the like, or any combination thereof. Using an inhaler for inhaling a drug has the advantage that when the liquid composition is inhaled, the drug is fast absorbed by the blood in the lungs and other body parts, thus improving the pharmacokinetics properties of the drug(s) compared inter alia to an oral intake of the same drug(s).

In accordance with another embodiment, the container further comprises a wick and wherein the wick is at least partially soaked in the liquid composition comprised in the container.

By still a further embodiment, the container comprises a first cavity for holding that liquid composition, and at least one other cavity for holding one or more different materials.

The container may be included within the mobile inhaler as well as a vibration generator (e.g. a piezo-electric vibration generator) connected to an electrical conduit, in order to have a ready-to-use mobile inhaler. A complete vibrating mesh type nebulizer is therefore part of such a container. By making vibration generator part of the container, it is used with one container only. Thus, the risk of having a broken or a malfunctioning vibration generator, is substantially reduced. Yet, in case the vibration generator does not function properly, the container can easily be replaced with an operative inhaler.

Also, the mesh may be provided as a part of the container and no additional vibrating plate is required at the mobile inhaler side. By providing a mesh plate of a nebulizer with the container, it can be assured that the mesh is properly associated with the container. Consequently, a reliable production of aerosols can be assured. Further, by using a mesh plate only for the liquid which is comprised in that one container, the risk of having a clogged plate is reduced as the plate would be used only for a limited number of times.

BRIEF DESCRIPTION OF THE DRAWINGS

For a more complete understanding of the present invention, reference is now made to the following detailed description taken in conjunction with the accompanying drawings wherein:

FIG. 1—is a schematic exploded sectional view of an inhaler according to an embodiment of the present invention;

FIG. 2A—is a top view of the nebulizer of the FIG. 1;

FIG. 2B—is a side view of the nebulizer of the FIG. 1;

FIG. 3—is a schematic sectional view of a container according to an embodiment of the present invention;

FIG. 4—is a schematic sectional view of an alternative container according to another embodiment of the present invention;

FIG. 5—is a simplified sectional view of a mouthpiece with a heating coil;

FIG. 6—is a schematic sectional view of an inhaler according to yet another embodiment of the present invention;

FIG. 7—is a schematic sectional view of an inhaler according to a further embodiment of the present invention;

FIG. 8—is a schematic sectional view of still another embodiment of the present invention; and FIG. 9—is a schematic view illustrating another embodiment of the present invention, where the mobile inhaler is a single integral device.

DETAILED DESCRIPTION

In this disclosure, the term "comprising" is intended to have an open-ended meaning so that when a first element is stated as comprising a second element, the first element may also include one or more other elements that are not necessarily identified or described herein, or recited in the claims.

In the following description, for the purposes of explanation, numerous specific details are set forth in order to provide a better understanding of the present disclosure by way of examples. It should be apparent, however, that the present invention may be practiced without these specific details.

As a general remark, it is noted that for sake of clarity, in the present description and the drawings, the same reference numerals are used for corresponding elements of different embodiments.

FIG. 1 illustrates an exploded view of a mobile inhaler construed according to an embodiment of the present invention. The mobile inhaler comprises a mouthpiece 1 and a body element 2 which, when joined together form an elongated housing. The housing exemplified herein is in the shape of an e-cigarette with a substantially cylindrical shape.

Mouthpiece 1 and body element 2 according to this embodiment are screwed together. Alternatively, the mouthpiece 1 and the element 2 may be attached together through magnets or a bayonet mount to assemble an inhaler, or by implementing any other method known in the art per se.

Nebulizer 3 is arranged inside the mouthpiece 1 and is described in more details hereinafter when referring to FIGS. 2A and 2B.

Liquid container 4 is arranged, when the mouthpiece 1 and the body element are assembled to form the mobile inhaler, in a receptacle 5 of the mouthpiece 1 and/or body element 2. The container 4 is described in more details hereinafter when describing FIGS. 4 and 5.

In body element 2 there are arranged a power conversion circuit 6, a vacuum sensor 7, a control unit 8, a battery 9, a charging circuit 10 and a charging port 11.

In this embodiment, the nebulizer 3 is arranged in the mouthpiece 1 adjacent to inhaling opening 12 of mouthpiece 1. An inhaling channel 13 is schematically indicated by the dotted lines.

Nebulizer 3 is shown in more details in the FIGS. 2A and 2B. The nebulizer 3 is of the active mesh type and comprises a vibrating plate 14 in a shape of a disc. Mesh plate 14 has a central, dome-shaped circular region 15 provided with a plurality of openings. Mesh plate 14 is attached to a lower side of an annular piezo-electric vibration generator 17, wherein the dome-shaped region is aligned with the central hole of the vibration generator 17. Power supply cables 18 are connected with the vibration generator 17 and, upon assembly of the mouthpiece 1 with the body element 2, provide a connection with the power conversion unit 6 arranged in the body element 2.

The vibrating plate 14 is provided with 1,900 openings, each having an egress diameter of between 2.0 μm and 3.0 μm, wherein the dome-shaped region 15 has a diameter of about 4 mm.

FIG. 3 illustrates a schematic view of an embodiment of the present invention of container 4.

Container 4 comprises a body 19 defining a cavity with an aperture 21. In this cavity, wick 22 (made for example of Japanese cotton or polymeric fibres) is arranged. The wick 22 extends over substantially the whole length of the body 19 from aperture 21 to the bottom of the body 19, which is closed by a plug 23. The wick 22 itself forms a cavity and a support structure 24 is arranged in the cavity for supporting wick 22. The support structure is preferably made of a polymer e.g. polycarbonate or nylon. Such an arrangement allows using the mobile inhaler where the container is comprised, irrespective of the spatial angel at which the mobile inhaler is held.

The cavity can be filled with a liquid to be inhaled. For filling the cavity, plug 23 and a spring 25 are removed or not yet assembled respectively. After the liquid is inserted into the cavity, it is sealingly closed with plug 23. The plug 23 is attached to the body 19 through a snap-fit. The spring 25 therefore biases the support structure 24 and the wick 22 towards aperture 21.

Figure 3:
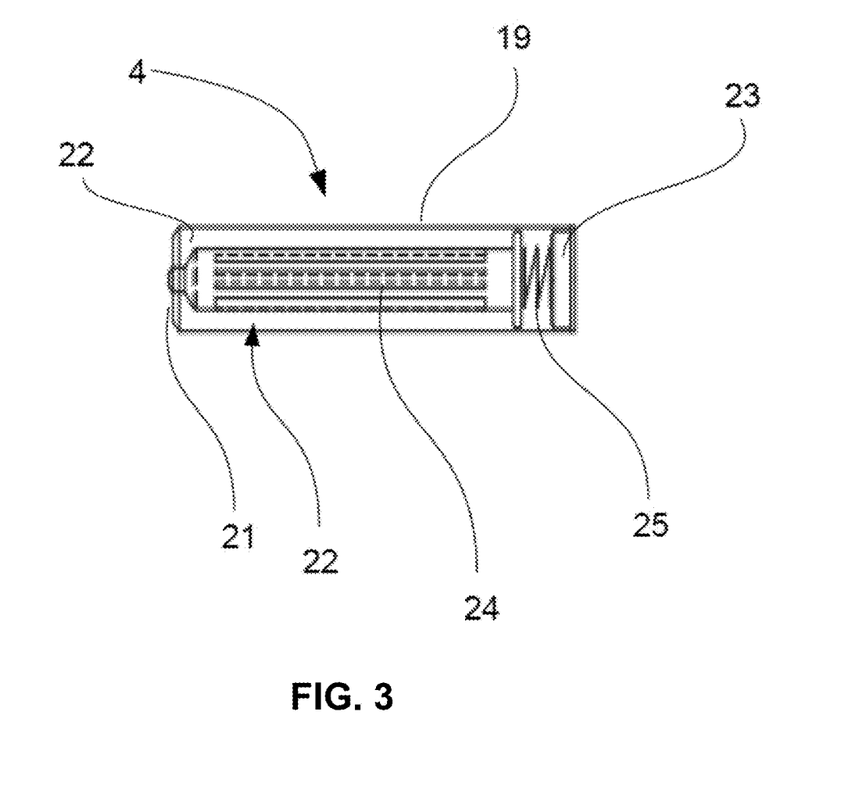
Figure 4:
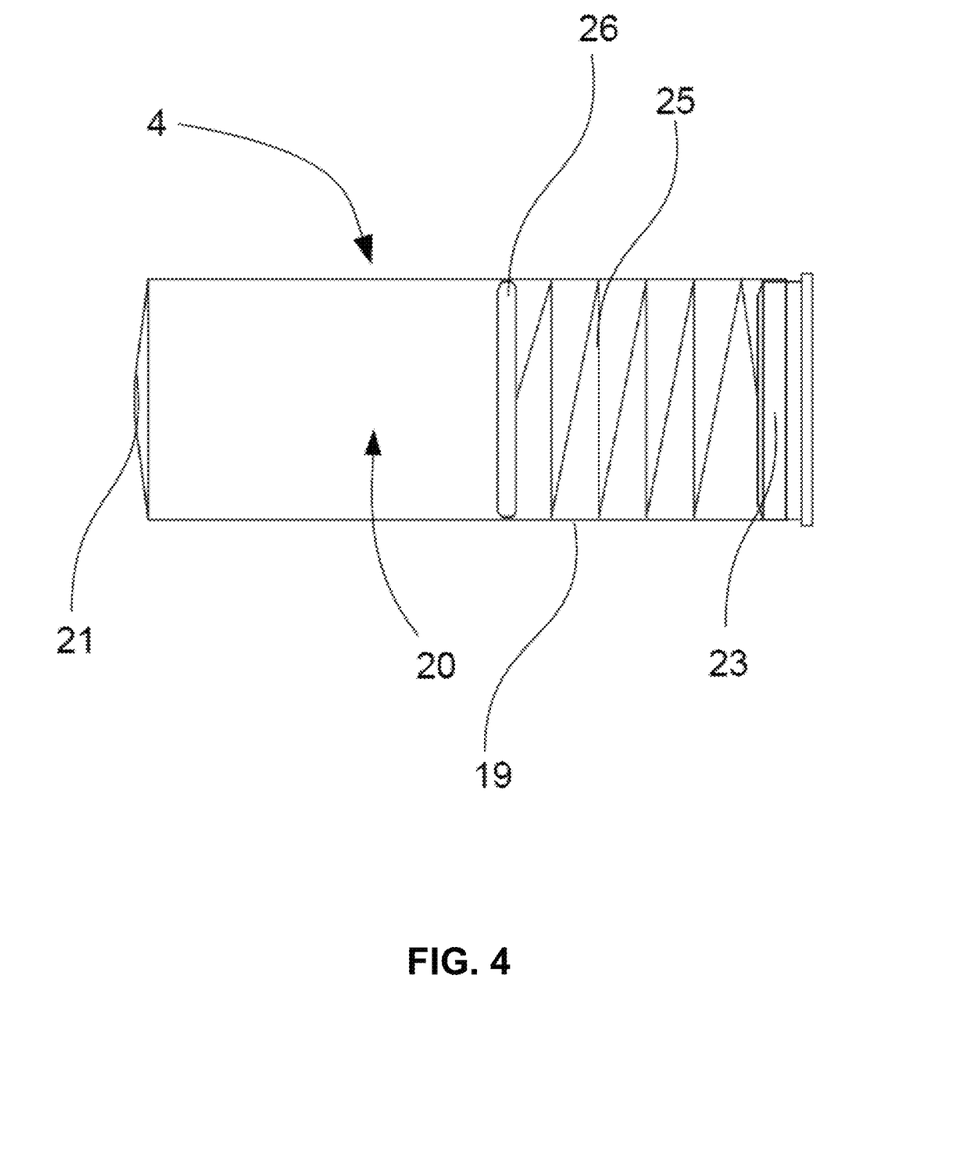

FIG. 4 illustrates schematically an alternative container 4 according to another embodiment of the invention. The embodiment of FIG. 4 is similar to the embodiment illustrated in FIG. 3 but comprises a piston 26 instead of an extended wick 22 (and a support structure 24).

Spring 25 is arranged between the piston 26 and the plug 23. After the cavity 20 is filled with liquid (not shown), piston 26 is inserted into the cavity and the cavity is then closed with the plug 23. The spring 25 biases the piston 26 towards the aperture 21.

In both embodiments, aperture 21 may be further closed by using a membrane (not shown) for sealing the container, which membrane may be peeled off by a user before inserting container 4 into the mobile inhaler, or perforated or otherwise removed/damaged (e.g. while closing the device or as a result of inserting the container in the mobile inhaler's enclosure, and the like) in order to assure a fluid connection between the content of container 4 and nebulizer 3.

When the inhaler is assembled with a container 4 (a capsule) located inside the receptacle of the mouthpiece 1 and the body element 2, aperture 21 is located adjacent to nebulizer 3, more precisely, adjacent to the nebulizer mesh.

Wick 22 is soaked with the liquid and ensures that the vibrating mesh plate 14 and in particular the dome-shaped region 15 is in fluid connection with the content of container 4. In the case of container 4 of FIG. 3, spring 25 ensures that wick 22 is pushed towards vibrating plate 14. In the case of container 4 of FIG. 4, the piston assembly ensures, over the spring 25 that nebulizer 3 is always provided with liquid. In both cases vibrating plate (mesh) 14 can produce an aerosol irrespective of the spatial orientation of the mobile inhaler.

When the inhaler is assembled and a user starts inhaling through inhaling opening 12 of mouthpiece 1, the pressure inside the housing decreases. This pressure decrease is detected by vacuum sensor 7 and communicated to control unit 8, which in turn activates nebulizer 3 for a given time interval, and/or as long as the pressure within the housing is less than the atmospheric pressure. Air from the environment may enter the housing over charging port or special made holes, in order to compensate the pressure decrease. Container 4, power control circuit 6, vacuum sensor 7, control unit 8, battery 9 and charging circuit 10 are arranged within the housing such that air can flow past them from charging port 11 to the inhaling opening 12.

Due to the air flow passing by nebulizer 3, the aerosol produced by nebulizer 3 is inhaled by the user through the inhaling channel 12 and the inhaling opening 13.

Figure 5:
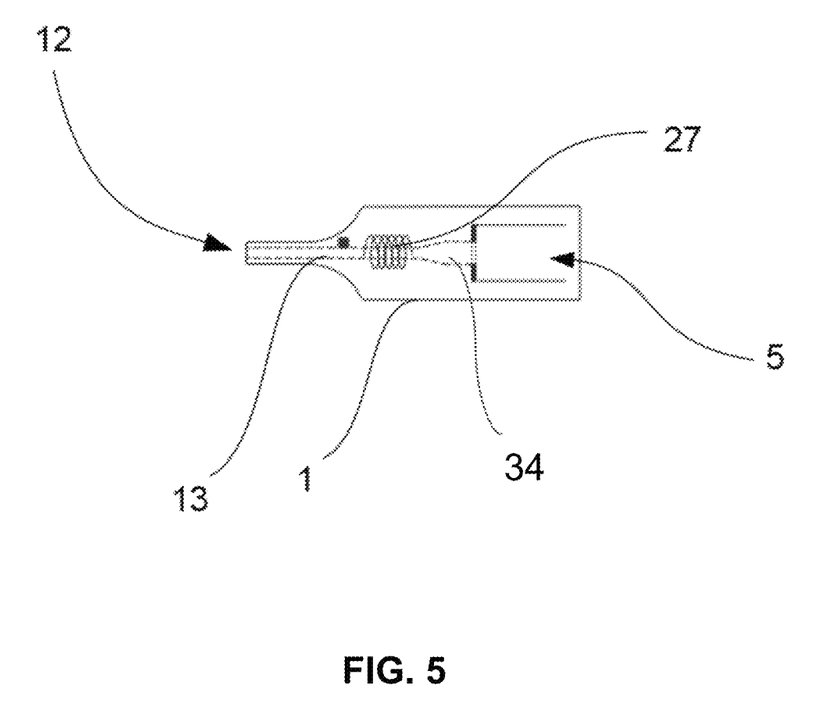

FIG. 5 illustrates an alternative embodiment of a mouthpiece 1 that comprises a heating coil 27. The heating coil 27 is schematically shown being able to heat the aerosol produced by a nebulizer 3 flowing through the inhaling channel 13. When the inhaler is assembled, the heating coil 27 is connected with a power source and control unit 8, and is only activated when a user is inhaling the aerosol. Heating coil 27 is configured to ensure that the aerosol which eventually be inhaled by the user, is heated up to a predetermined temperature, while ensuring that no change occurs in the chemical properties of the substance being inhaled.

The predetermined temperature is less than 100° C., and preferably it is one that is comfortable for the user body, e.g. 37° C.±4° C.

Figure 6:
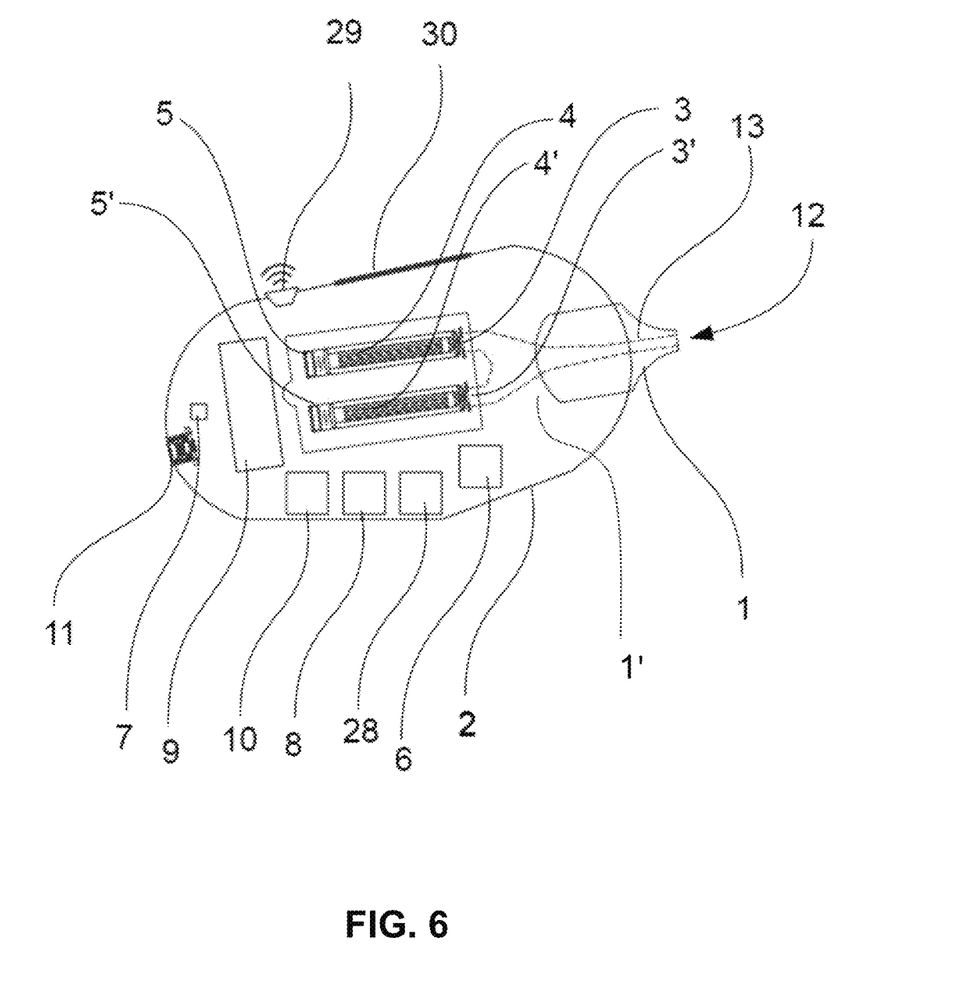

Another embodiment of the present invention of a mobile inhaler is schematically presented in FIG. 6.

The mobile inhaler comprises a mouthpiece 1, shown in a use position, having an inhaling opening 12 which is slidably arranged in a body element 2 between a rest position 1' and a use position. The body element is designed as a handheld device that can be easily held in a user's hand.

The inhaler also comprises two receptacles 5 and 5', each for a respective container 4 and 4' containing a liquid drug solution.

Figure 2A:
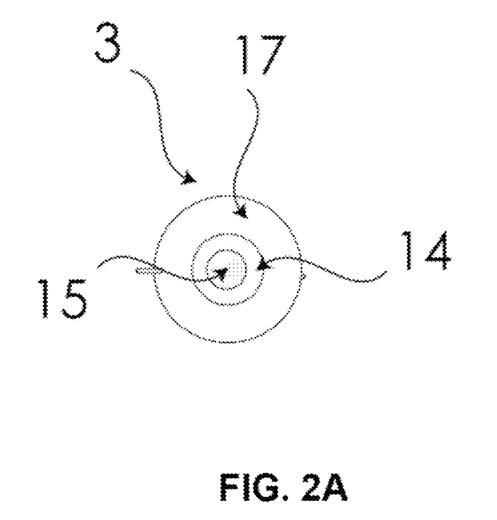
Figure 2B:
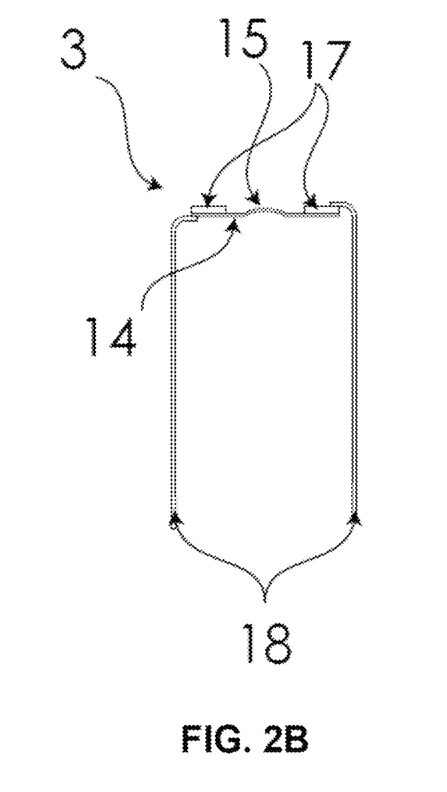

Each of the containers 4 is in fluid connection with respective nebulizers 3 and 3' of the active mesh type as described above and shown in FIGS. 2A and 2B. The nebulizers 3 and 3' are arranged between the respective container 4 and 4' and mouthpiece 1. An inhaling channel 13 connects the flow paths of the two nebulizers 3 and 3' and leads to an inhaling opening 12 of mouthpiece 1.

The inhaler also comprises a power conversion circuit 6, a vacuum sensor 7, a control unit 8, a battery 9, a charging circuit 10 and a charging port 11.

The inhaler of this example further comprises a communication unit 28, a speaker 29 and a display 30, being in data communication with control unit 8.

Figure 1:
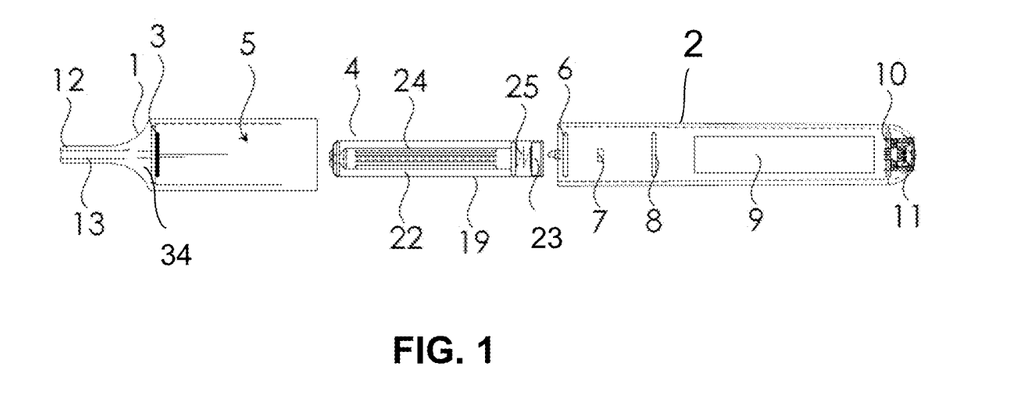

The inhaler is generally operated as explained hereinabove with respect to the mobile inhaler of the FIG. 1, but may be more suitable for the inhalation of different drugs according to a predefined medication scheme.

Communication unit 28 enables communication of different data between the mobile inhaler and a remote device.

A possible mode of operation of the mobile inhaler will now be described. Since the principle of operation is similar, the invention will be described with reference to container 4. However, it should be understood that the same also applies to the use of container 4' mutatis mutandis, as well as for enclosures which do not have a detachable container comprised therein (i.e. in cases where liquid is inserted directly to the enclosure).

First, container 4 is inserted into the inhaler. The container 4 contains information about the content of the container, concentration of the drug, etc. This information is transmitted to the mobile inhaler by means of e.g. an RFID system (not shown) or a barcode (not shown) or an electronic storage (e.g. as in a credit card) and is stored in a memory of the mobile inhaler.

A health professional such as a physician or a pharmacist can then program the predefined medication scheme into the mobile inhaler via communication unit 28. In addition, progress reports and updates may be sent to the user's physician and/or insurance company.

In this example, let us assume that the medication scheme comprises two scheduled inhalations of a predetermined dose of the drug during the day at predefined times (e.g. 8 AM and 8 PM).

When control unit 8 detects that the scheduled inhalation should be performed, it triggers an alert for the user, so that by hearing a tone emitted by speaker 29, the user becomes aware that it is time for him/her to carry out the inhalation procedure.

As soon as mouthpiece 1 is moved from its rest position to the inhaling position, the mobile inhaler is activated from a standby mode and is ready for operation.

The user then starts inhaling and, as described above with respect to the inhaler of FIG. 1, nebulizer 3 is triggered by control unit 8 to emit a predefined quantity of aerosol. The quantity of aerosol produced by nebulizer is calculated by the control unit 8 such that the predefined drug dose is inhaled. After the predefined dose of the drug has been inhaled, speaker 29 emits a tone, notifying the user that he may stop inhaling.

The user then slides the mouthpiece 1 back to the rest position and consequently the device enters a standby mode.

Data which relates to the inhalation procedure that took place, such as inhaling time, inhaled quantity, etc. is then stored in the memory of the mobile inhaler and is then transmitted (at some stage) via communication unit 28 to a remote device. Thus, it is possible for the physician either in real-time or by checking the stored data during the patient visit, to check whether the patient has been following the medication scheme prescribed or not. In addition, the concern of overdosing or wrong dosing of the drug can be eliminated since it is not possible for a user to inhale two times a dose within a period of time shorter than the one determined for him/her.

This procedure is then repeated every day at 8 AM and 8 PM, as long as the predefined medication scheme has not been terminated.

Moreover, it should be understood that carrying out a mixed medication scheme of administering a first drug contained in container 4 and a second drug contained in the container 4', is also possible. Furthermore, both drugs may be inhaled simultaneously, where each nebulizer 3 and 3' is triggered independently in order to deliver the predetermined drug dose.

Display 30 may be used to provide the user with different information such as the status of the mobile inhaler, battery level, countdown until the next inhalation is due, etc.

Figure 7:
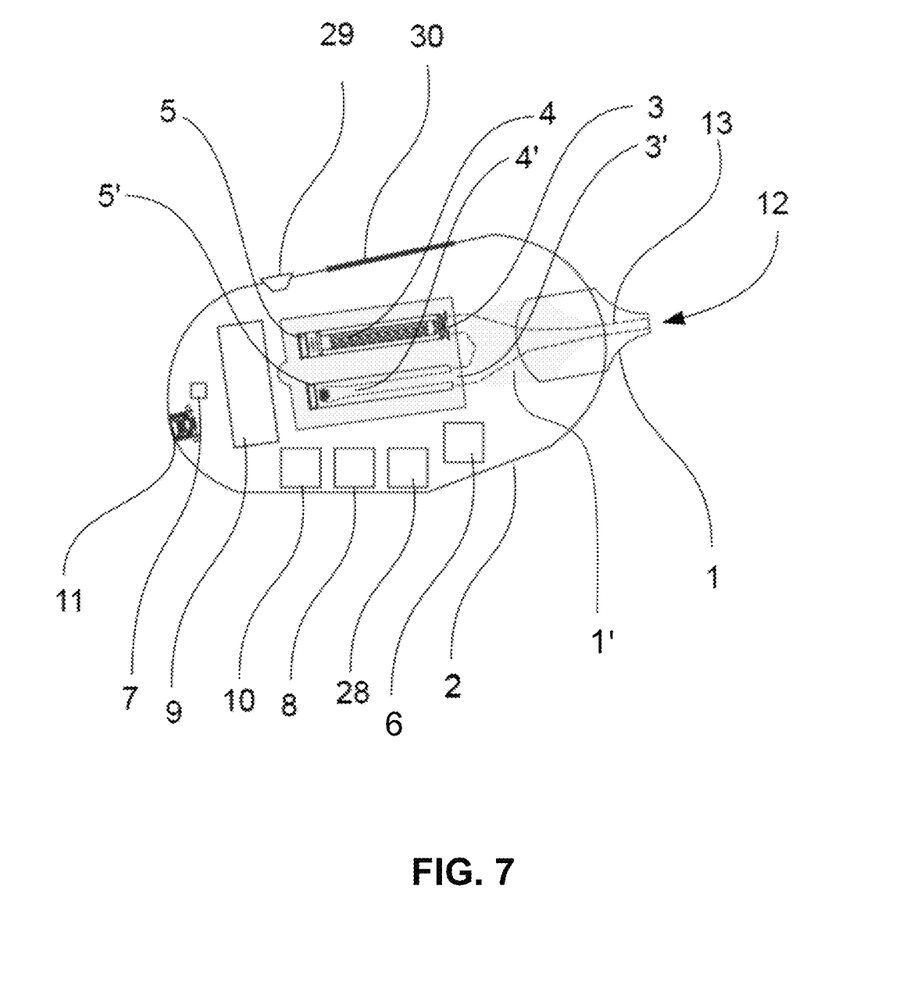

The inhaler illustrated in the FIG. 7 is similar to the inhaler shown in FIG. 6 with the exception that capsule 4' is of a different type as nebulizer 3' is of the heating coil type. One optional way of implementing this example is when container 4 comprises nicotine solution, and container 4' comprises aroma agent. By vaporizing the aroma agent comprised in container 4', the vapours thus obtained may be inhaled together with the nicotine containing aerosol derived from container 4, and consequently the user is subjected to an improved experience due to this combination.

Figure 8:
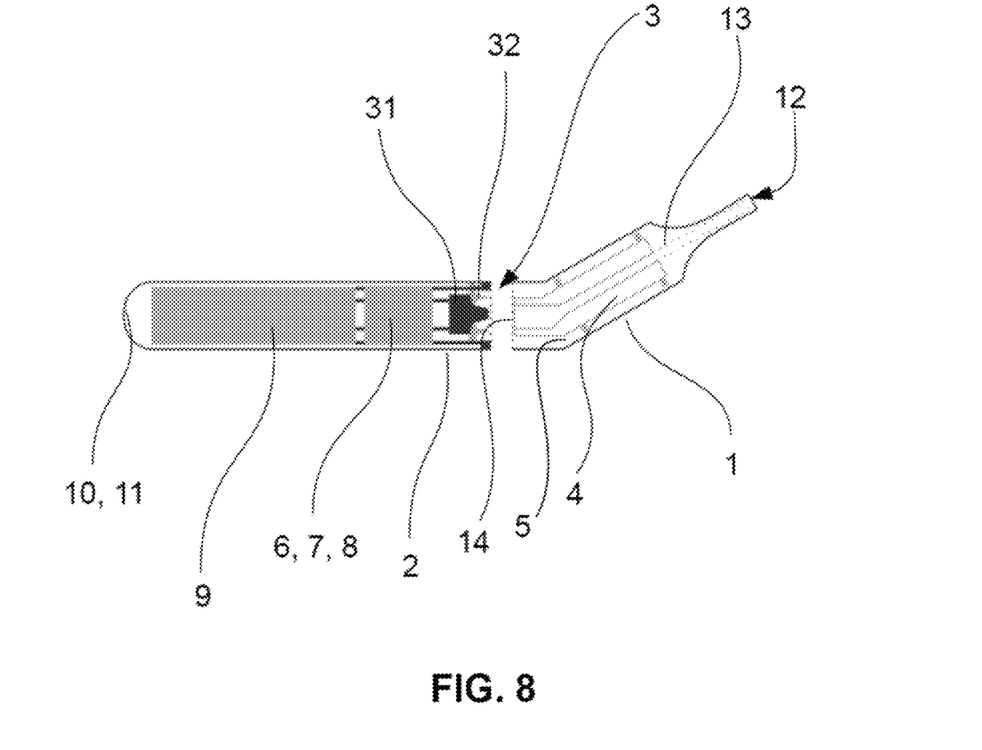

In FIG. 8 another embodiment of a mobile inhaler construed according to the present invention, is illustrated.

The mobile inhaler comprises a mouthpiece 1 and a body element 2 which, when joined together form an elongated housing. The housing is preferably in the shape of a pipe and is shown schematically in FIG. 8 by the bend shape.

Mouthpiece 1 and body element 2 are screwed together. Alternatively, mouthpiece 1 and element 2 may be attached together through magnets or a bayonet mount to assemble the mobile inhaler.

A liquid container 4 is inserted, when mouthpiece 1 and body element are assembled to form the mobile inhaler, in a receptacle 5 of mouthpiece 1.

In body element 2 there are also arranged a power conversion circuit 6, a vacuum sensor 7, a control unit 8, a battery 9, a charging circuit 10 and a charging port 11.

Nebulizer 3 of this example is of the passive mesh type and comprises a transducer horn 31 attached to a piezoelectric vibration generator located within the body element 2, while mesh 14 with a plurality of openings is attached to the container 4 at the end of the container, located near the tip of transducer horn 31 when the mobile inhaler is assembled. Mesh 14 is therefore disposable with the container 4.

Perforation spikes 32 may optionally be located adjacent to transducer horn 31 such that, when mouthpiece 1 is connected to body element 2, a connection part of container 4 is perforated by perforation spikes 32. The liquid contained in container 4 can therefore fill the space located between transducer horn 31 and mesh plate 14. Since the mobile inhaler is designed as a pipe and is used with container 4 being in a tilted position, liquid contained in container 4 is always provided to transducer horn 31 when the inhaler is operative.

Container 4 is designed with a ring shaped cross section such that an aerosol channel 34 extending throughout the whole length of the container 4 is formed. The mesh plate 14 is arranged at the end of container 4 not facing the inhaling channel 13 and the inhaling opening 12, and is aligned with the aerosol channel of container 4. The aerosol channel is connected to inhaling channel 13 of mouthpiece 1 leading to inhaling opening 12.

When the mobile inhaler is activated by inhaling as described above with respect to other embodiments of the present invention, the aerosol generated by nebulizer 3 may flow with air coming from air inlets (not shown) through the aerosol channel 34 and the inhaling channel 13, to the mouth of a user.

Figure 9:
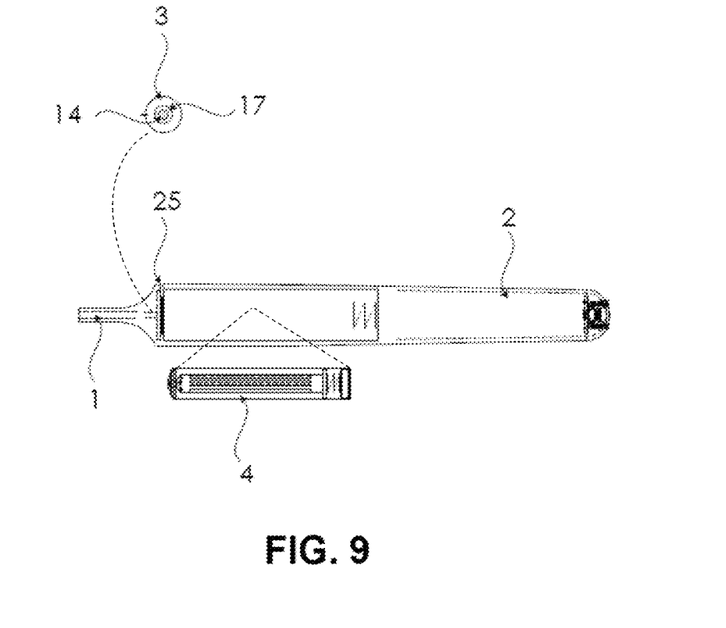

FIG. 9 illustrates an exploded view of a mobile inhaler construed according to another embodiment of the present invention. Unlike the embodiment illustrated in FIG. 1 wherein the mobile inhaler comprises a mouthpiece 1 and a body element 2 which, when joined together form an elongated housing, the mobile inhaler illustrated in FIG. 9 comprises a single piece that comprises both mouthpiece 1 and body element 2.

Nebulizer 3 which comprises mesh plate 14 and ultrasonic vibration generator 17 is located at upper part of body element 2 (location indicated by numeral 25) of the mobile inhaler, and liquid container 4 is detachably insertable into a suitable housing of body element 2.

All examples and conditional language recited herein are intended for assessing the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

A person skilled in the art will readily note that other embodiments of the disclosure may be achieved without departing from the scope of the disclosure. All such embodiments are included herein. The scope of the disclosure should be limited solely by the claims thereto.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The invention claimed is:
1. A mobile inhaler device, comprising:
a mouthpiece comprising at least one inhaling opening;
a body element connected to the mouthpiece and comprising a housing for holding a DC power source;

an enclosure holding a container that comprises a liquid in a cavity, wherein the container comprises a wick arranged in the cavity in contact with the liquid;

a power conversion unit comprising an inverter operative to convert a DC voltage provided by a DC power source, into a higher AC voltage;

a nebulizer comprising an ultrasonic vibrator and a mesh, the mesh having a disc shape and comprising a central, dome-shaped circular region having a convex side arranged to extend towards the at least one inhaling opening, the dome-shaped circular region comprising a plurality of openings, wherein the mesh is configured to be in contact with the wick, thereby preventing direct contact between the mesh and the liquid, wherein said ultrasonic vibrator is configured to vibrate the mesh and be activated by said AC voltage, and wherein the ultrasonic vibrator is an annular piezo-electric vibration generator, and wherein the mesh is directly attached to a lower side of the annular piezo-electric vibration generator and the dome-shaped circular region is aligned with a central hole of the vibration generator, and wherein said nebulizer is adapted to enable converting at least part of the liquid into aerosol droplets, and wherein the aerosol droplets are capable of being directly inhaled from said mouthpiece; and wherein the enclosure is adapted to enable holding the liquid, and characterized in that the enclosure provides a connection to enable fluid transfer for said enclosure to the nebulizer, wherein:

the wick forms a second cavity and a support structure is arranged in the second cavity for supporting the wick; and the arrangement of the wick and the support structure enables fluid transfer from the enclosure to the nebulizer irrespective of a spatial angle at which the mobile inhaler device is being held.

2. The mobile inhaler device of claim 1, characterized in that the mobile inhaler device is configured to enable inhaling aerosol droplets derived from over 60% of an initial volume of the liquid held within said enclosure.

3. The mobile inhaler device of claim 1, wherein the mouthpiece is detachably connected to the body element, and wherein the nebulizer is comprised within the mouthpiece.

4. The mobile inhaler device of claim 1, wherein the mesh is fixedly positioned in said mobile inhaler device, and wherein said ultrasonic vibrator is operative to enable conveying liquid held in the enclosure towards said mesh.

5. The mobile inhaler device of claim 1, wherein at least two of the openings included in said plurality of openings have different dimensions from each other.

6. The mobile inhaler device of claim 1, further comprising an electrical circuit for increasing AC voltage provided to said ultrasonic vibrator, and wherein:

the electrical circuit enables control an amount of liquid converted into aerosol droplets, by changing the AC voltage provided, and the electrical circuit comprises at least one member of the group that consists of a resonant circuit and a phase-locked loop (PLL).

7. The mobile inhaler device of claim 1, further including a vacuum sensor configured to affect operation of said mobile inhaler device, wherein:

said vacuum sensor controls an amount of aerosol being inhaled by a user of said mobile inhaler device, and wherein the amount of liquid converted into aerosol droplets depends on a vacuum pressure level at said mobile inhaler device.

8. The mobile inhaler device of claim 1, further comprising a heating element adapted to enable increasing a temperature of the aerosol droplets prior to egress of the droplets via the mouthpiece.

9. The mobile inhaler device of claim 1, wherein the mouthpiece is movable between a rest position and a use position, wherein in the rest position, the mouthpiece is at least partially accommodated into the body element.

10. The mobile inhaler device of claim 1, further including a communication interface for transferring and receiving information between the mobile inhaler device and a remote electronic device.

11. The mobile inhaler device of claim 1, further comprising a control unit.

12. The mobile inhaler device of claim 1, further including a display for providing information to a user of said mobile inhaler device.

13. The mobile inhaler device of claim 1, further comprising a switch to prevent unauthorized use of the mobile inhaler device.

14. The mobile inhaler device of claim 1, further comprising at least one additional enclosure for holding at least one additional liquid, and a vaporizer operative to selectively vaporize one or more of the at least one additional liquid.

15. The mobile inhaler device of claim 1, wherein said enclosure is configured to enable holding the container that comprises the liquid of said mobile inhaler device, wherein said enclosure or said container which is detachably associated with said enclosure, includes a piston, wherein the container is located at least partially inside the mouthpiece and is disposable, and wherein the nebulizer mesh is comprised within said container.

16. The mobile inhaler device of claim 15, further comprising a communication interface for receiving information about the liquid stored in said container.

17. The mobile inhaler device of claim 15, further comprising a spring operative to enable biasing the container and/or the nebulizer towards each other.

18. The mobile inhaler device of claim 1, wherein:

the cavity of the container has an aperture at a first end thereof, a plug is located at a second end of the cavity and the second end is opposite to the first end; and the plug is sealingly engaged with the second end of the cavity by a snap-fit.

19. The mobile inhaler device of claim 1, wherein the mobile inhaler device further comprises a user identification device comprising a fingerprint reader to prevent unauthorized use of the mobile inhaler device.

20. The mobile inhaler device of claim 1, wherein the mobile inhaler device further comprises a control unit configured to:

detect a time for a scheduled inhalation by a user of the mobile inhaler device; and trigger an audio alert for the user at the time of the scheduled inhalation so that the user becomes aware that it is time to carry out the scheduled inhalation.

* * * * *